United States Patent
Lambrecht et al.

(10) Patent No.: US 12,310,691 B2
(45) Date of Patent: May 27, 2025

(54) MULTI-CABLE MEDICAL INSTRUMENT

(71) Applicant: Intuitive Surgical Operations, Inc., Sunnyvale, CA (US)

(72) Inventors: Bram Gilbert Antoon Lambrecht, Redwood City, CA (US); S. Christopher Anderson, San Francisco, CA (US); Ladd T. Johnson, Scotts Valley, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/591,811

(22) Filed: Feb. 29, 2024

(65) Prior Publication Data
US 2024/0315792 A1 Sep. 26, 2024

Related U.S. Application Data

(63) Continuation of application No. 17/529,967, filed on Nov. 18, 2021, now Pat. No. 11,950,873, which is a
(Continued)

(51) Int. Cl.
*A61B 34/00* (2016.01)
*A61B 34/30* (2016.01)
(Continued)

(52) U.S. Cl.
CPC .............. *A61B 34/71* (2016.02); *A61B 34/00* (2016.02); *A61B 34/30* (2016.02);
(Continued)

(58) Field of Classification Search
CPC ......... A61B 34/71; A61B 34/00; A61B 34/30; A61B 17/29; A61B 2017/00477;
(Continued)

(56) References Cited

U.S. PATENT DOCUMENTS

| 793,510 A | 6/1905 | Cramer et al. |
|---|---|---|
| 2,091,317 A | 8/1937 | Hill |

(Continued)

FOREIGN PATENT DOCUMENTS

| AU | 2014208189 A1 | 4/2015 |
|---|---|---|
| CN | 101893060 A | 11/2010 |

(Continued)

OTHER PUBLICATIONS

Extended European Search Report for Application No. EP17828154.9 mailed on Jun. 24, 2020, 11 pages.
(Continued)

*Primary Examiner* — Ankit D Tejani
*Assistant Examiner* — Joshua Brendon Solomon

(57) ABSTRACT

A medical instrument includes cable pairs respectively wound around input spindles and connected to actuate degrees of freedom of an instrument shaft structure. The cables may connect so that rotating the input spindles actuates corresponding degrees of freedom. First pulleys in the instrument may receive first cables from the input spindles and redirect the first cables toward the instrument shaft, and second pulleys may receive second cables from the input spindles and redirect the second cables toward the instrument shaft. In one configuration, the first and second pulleys are respectively mounted at first and second levels, and the second pulleys redirect the second cables through the first level. Additionally or alternatively, one level of cables may cross while the other level of cables does not.

16 Claims, 6 Drawing Sheets

Related U.S. Application Data continuation of application No. 16/317,235, filed as application No. PCT/US2017/038674 on Jun. 22, 2017, now Pat. No. 11,207,145.

(60) Provisional application No. 62/362,431, filed on Jul. 14, 2016.

(51) Int. Cl.
    *A61B 17/00* (2006.01)
    *A61B 17/29* (2006.01)
    *A61B 90/00* (2016.01)

(52) U.S. Cl.
    CPC ..... *A61B 2017/00477* (2013.01); *A61B 17/29* (2013.01); *A61B 2017/2903* (2013.01); *A61B 2017/2929* (2013.01); *A61B 2034/715* (2016.02); *A61B 2090/371* (2016.02)

(58) Field of Classification Search
    CPC .... A61B 2017/2903; A61B 2017/2929; A61B 2034/715; A61B 2090/371
    See application file for complete search history.

(56) References Cited

U.S. PATENT DOCUMENTS

| | | |
|---|---|---|
| 2,186,181 A | 1/1940 | Gustav et al. |
| 3,618,420 A | 11/1971 | Horwitt et al. |
| 4,084,594 A | 4/1978 | Mosior |
| 4,341,144 A | 7/1982 | Milne |
| 4,899,608 A | 2/1990 | Knappe et al. |
| 5,207,691 A | 5/1993 | Nardella |
| 5,352,235 A | 10/1994 | Koros et al. |
| 5,792,135 A | 8/1998 | Madhani et al. |
| 5,807,377 A | 9/1998 | Madhani et al. |
| 5,817,128 A | 10/1998 | Storz |
| 5,876,325 A | 3/1999 | Mizuno et al. |
| 6,007,550 A | 12/1999 | Wang et al. |
| 6,331,181 B1 | 12/2001 | Tierney et al. |
| 6,371,952 B1 | 4/2002 | Madhani et al. |
| 6,394,998 B1 | 5/2002 | Wallace et al. |
| 6,676,684 B1 | 1/2004 | Morley et al. |
| 6,817,974 B2 | 11/2004 | Cooper et al. |
| 6,994,708 B2 | 2/2006 | Manzo |
| 7,048,745 B2 | 5/2006 | Tierney et al. |
| 7,090,683 B2 | 8/2006 | Brock et al. |
| 7,169,141 B2 | 1/2007 | Brock et al. |
| 7,214,230 B2 | 5/2007 | Brock et al. |
| 7,331,967 B2 | 2/2008 | Lee et al. |
| 7,371,210 B2 | 5/2008 | Brock et al. |
| 7,524,320 B2 | 4/2009 | Tierney et al. |
| 7,582,055 B2 | 9/2009 | Komiya et al. |
| 7,608,056 B2 | 10/2009 | Kennedy, II et al. |
| 7,608,083 B2 | 10/2009 | Lee et al. |
| 7,666,191 B2 | 2/2010 | Orban, III et al. |
| 7,935,130 B2 | 5/2011 | Williams |
| 8,224,484 B2 | 7/2012 | Swarup et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,597,280 B2 | 12/2013 | Cooper et al. |
| 8,771,270 B2 | 7/2014 | Burbank |
| 8,800,838 B2 | 8/2014 | Shelton, IV |
| 8,808,166 B2 | 8/2014 | Hosaka |
| 8,821,480 B2 | 9/2014 | Burbank |
| 8,911,471 B2 | 12/2014 | Spivey et al. |
| 8,992,565 B2 | 3/2015 | Brisson et al. |
| 9,028,494 B2 | 5/2015 | Shelton, IV et al. |
| 9,078,684 B2 | 7/2015 | Williams |
| 9,204,923 B2 | 12/2015 | Manzo et al. |
| 9,232,979 B2 | 1/2016 | Parihar et al. |
| 9,259,274 B2 | 2/2016 | Prisco |
| 9,572,616 B2 | 2/2017 | Vaughn |
| 9,839,439 B2 | 12/2017 | Cooper et al. |
| 9,869,339 B2 | 1/2018 | Zimmerman et al. |
| 9,931,106 B2 | 4/2018 | Au et al. |
| 9,962,066 B2 | 5/2018 | Rogers et al. |
| 10,130,366 B2 | 11/2018 | Shelton, IV et al. |
| 10,219,874 B2 | 3/2019 | Yu et al. |
| 10,288,837 B2 | 5/2019 | Miyatani et al. |
| 10,299,873 B2 | 5/2019 | Hares et al. |
| 10,314,583 B2 | 6/2019 | Smith et al. |
| 10,357,321 B2 | 7/2019 | Donlon et al. |
| 10,550,918 B2 | 2/2020 | Cooper et al. |
| 10,595,948 B2 | 3/2020 | Solomon et al. |
| 10,595,949 B2 | 3/2020 | Donlon et al. |
| 10,682,141 B2 | 6/2020 | Moore et al. |
| 10,779,898 B2 | 9/2020 | Hill et al. |
| 10,806,530 B2 | 10/2020 | Liao et al. |
| 10,813,706 B2 | 10/2020 | Chaplin et al. |
| 10,932,868 B2 | 3/2021 | Solomon et al. |
| 11,013,566 B2 | 5/2021 | Diel et al. |
| 11,129,686 B2 | 9/2021 | Chaplin et al. |
| 11,207,145 B2 | 12/2021 | Lambrecht et al. |
| 11,241,290 B2 | 2/2022 | Waterbury et al. |
| 11,248,686 B2 | 2/2022 | Cooper et al. |
| 11,304,770 B2 | 4/2022 | Crews et al. |
| 11,517,397 B2 | 12/2022 | Lambrecht et al. |
| 2002/0111635 A1 | 8/2002 | Jensen et al. |
| 2003/0068607 A1* | 4/2003 | Gregorio .............. A61B 34/70 434/262 |
| 2005/0119527 A1 | 6/2005 | Banik et al. |
| 2006/0074415 A1 | 4/2006 | Scott et al. |
| 2006/0217742 A1 | 9/2006 | Messerly et al. |
| 2006/0276775 A1 | 12/2006 | Rosenberg et al. |
| 2007/0043338 A1 | 2/2007 | Moll et al. |
| 2007/0119274 A1 | 5/2007 | Devengenzo et al. |
| 2007/0137371 A1 | 6/2007 | Devengenzo et al. |
| 2007/0232858 A1 | 10/2007 | Macnamara et al. |
| 2008/0009838 A1 | 1/2008 | Schena et al. |
| 2008/0015566 A1 | 1/2008 | Livneh |
| 2008/0046122 A1 | 2/2008 | Manzo et al. |
| 2008/0065102 A1 | 3/2008 | Cooper |
| 2008/0065105 A1 | 3/2008 | Larkin et al. |
| 2008/0087871 A1 | 4/2008 | Schena et al. |
| 2008/0103491 A1 | 5/2008 | Omori et al. |
| 2008/0125794 A1 | 5/2008 | Brock et al. |
| 2008/0196533 A1 | 8/2008 | Bergamasco et al. |
| 2009/0088774 A1 | 4/2009 | Swarup et al. |
| 2009/0198272 A1 | 8/2009 | Kerver et al. |
| 2009/0222022 A1 | 9/2009 | Laporte et al. |
| 2010/0011900 A1 | 1/2010 | Burbank et al. |
| 2010/0170519 A1 | 7/2010 | Romo et al. |
| 2010/0175701 A1 | 7/2010 | Reis et al. |
| 2010/0198253 A1 | 8/2010 | Jinno et al. |
| 2010/0318101 A1 | 12/2010 | Choi et al. |
| 2011/0015650 A1 | 1/2011 | Choi et al. |
| 2011/0065992 A1 | 3/2011 | Bissinger |
| 2011/0118754 A1 | 5/2011 | Dachs, II et al. |
| 2011/0184241 A1 | 7/2011 | Zubiate et al. |
| 2011/0277580 A1 | 11/2011 | Cooper et al. |
| 2011/0277775 A1 | 11/2011 | Holop et al. |
| 2011/0295269 A1 | 12/2011 | Swensgard et al. |
| 2011/0295270 A1 | 12/2011 | Giordano et al. |
| 2012/0046522 A1 | 2/2012 | Naito |
| 2012/0123441 A1 | 5/2012 | Au et al. |
| 2012/0150192 A1 | 6/2012 | Dachs, II et al. |
| 2012/0239060 A1 | 9/2012 | Orban, III et al. |
| 2012/0289974 A1 | 11/2012 | Rogers et al. |
| 2012/0292367 A1 | 11/2012 | Morgan et al. |
| 2012/0298719 A1 | 11/2012 | Shelton, IV et al. |
| 2013/0046318 A1 | 2/2013 | Radgowski et al. |
| 2013/0144395 A1 | 6/2013 | Stefanchik et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0039527 A1 | 2/2014 | Avelar et al. |
| 2014/0107665 A1 | 4/2014 | Shellenberger et al. |
| 2014/0114327 A1 | 4/2014 | Boudreaux et al. |
| 2014/0257333 A1 | 9/2014 | Blumenkranz |
| 2014/0309625 A1 | 10/2014 | Okamoto et al. |
| 2015/0150635 A1 | 6/2015 | Kilroy et al. |

(56) References Cited

U.S. PATENT DOCUMENTS

| | | |
|---|---|---|
| 2015/0150636 A1 | 6/2015 | Hagn et al. |
| 2015/0157355 A1 | 6/2015 | Price et al. |
| 2016/0045770 A1 | 2/2016 | Yamada |
| 2016/0157926 A1 | 6/2016 | Boudreaux |
| 2016/0184034 A1 | 6/2016 | Holop et al. |
| 2016/0338762 A1 | 11/2016 | Krastins et al. |
| 2016/0361049 A1 | 12/2016 | Dachs, II et al. |
| 2016/0361107 A1 | 12/2016 | Zergiebel et al. |
| 2017/0007345 A1 | 1/2017 | Smith et al. |
| 2017/0165017 A1 | 6/2017 | Chaplin et al. |
| 2017/0207467 A1 | 7/2017 | Shelton, IV et al. |
| 2018/0055583 A1 | 3/2018 | Schuh et al. |
| 2018/0126504 A1 | 5/2018 | Shelton, IV et al. |
| 2018/0214223 A1 | 8/2018 | Turner |
| 2019/0125468 A1 | 5/2019 | Adams |
| 2019/0231464 A1 | 8/2019 | Wixey et al. |
| 2019/0374240 A1 | 12/2019 | Brodbeck et al. |
| 2020/0060516 A1 | 2/2020 | Baez, Jr. |
| 2020/0138473 A1 | 5/2020 | Shelton, IV et al. |
| 2020/0197117 A1 | 6/2020 | Donlon et al. |
| 2021/0322118 A1 | 10/2021 | Donlon et al. |
| 2022/0000572 A1 | 1/2022 | Ragosta et al. |
| 2022/0071727 A1 | 3/2022 | Lambrecht et al. |
| 2022/0192764 A1 | 6/2022 | Waterbury et al. |
| 2023/0079266 A1 | 3/2023 | Wixey et al. |
| 2023/0119001 A1 | 4/2023 | Abbott |
| 2023/0119775 A1 | 4/2023 | Lambrecht et al. |
| 2023/0279931 A1 | 9/2023 | Cooper et al. |
| 2023/0329807 A1 | 10/2023 | Heye |
| 2024/0090972 A1 | 3/2024 | Lambrecht et al. |
| 2024/0197423 A1 | 6/2024 | Ragosta et al. |
| 2024/0366329 A1 | 11/2024 | Kadokura |
| 2024/0382279 A1 | 11/2024 | Baldwin et al. |

FOREIGN PATENT DOCUMENTS

| | | |
|---|---|---|
| CN | 102100569 A | 6/2011 |
| CN | 102292046 A | 12/2011 |
| CN | 103240732 A | 8/2013 |
| CN | 104116547 A | 10/2014 |
| CN | 104799891 A | 7/2015 |
| CN | 105058406 A | 11/2015 |
| CN | 109505951 A | 3/2019 |
| EP | 2362285 A2 | 8/2011 |
| EP | 2548529 A1 | 1/2013 |
| EP | 2783643 A1 | 10/2014 |
| EP | 2640301 B1 | 3/2016 |
| EP | 3103374 A1 | 12/2016 |
| EP | 3195993 A1 | 7/2017 |
| FR | 3014678 A1 | 6/2015 |
| JP | H06114000 A | 4/1994 |
| JP | H10249777 A | 9/1998 |
| JP | 2002200091 A | 7/2002 |
| JP | 2005288590 A | 10/2005 |
| JP | 2009500086 A | 1/2009 |
| JP | 5815081 B2 | 11/2015 |
| KR | 100778387 B1 | 11/2007 |
| WO | WO-8910242 A1 | 11/1989 |
| WO | WO-9729690 A1 | 8/1997 |
| WO | WO-0030557 A1 | 6/2000 |
| WO | WO-03001986 A2 | 1/2003 |
| WO | WO-2010009221 A2 | 1/2010 |
| WO | WO-2010009224 A1 | 1/2010 |
| WO | WO-2010081050 A1 | 7/2010 |
| WO | WO-2011060046 A2 | 5/2011 |
| WO | WO-2012064528 A1 | 5/2012 |
| WO | WO-2012068156 A2 | 5/2012 |
| WO | WO-2013118774 A1 | 8/2013 |
| WO | WO-2015142290 A1 | 9/2015 |
| WO | WO-2016161449 A1 | 10/2016 |
| WO | WO-2016172299 A1 | 10/2016 |
| WO | WO-2017064303 A1 | 4/2017 |
| WO | WO-2018013313 A1 | 1/2018 |
| WO | WO-2018049217 A1 | 3/2018 |
| WO | WO-2018069679 A1 | 4/2018 |
| WO | WO-2018094191 A1 | 5/2018 |
| WO | WO-2020102776 A1 | 5/2020 |
| WO | WO-2020102780 A1 | 5/2020 |
| WO | WO-2020252184 A1 | 12/2020 |
| WO | WO-2021155707 A1 | 8/2021 |
| WO | WO-2023055684 A2 | 4/2023 |
| WO | WO-2023177554 A1 | 9/2023 |

OTHER PUBLICATIONS

International Search Report and Written Opinion for Application No. PCT/US2017/038674, mailed on Oct. 31, 2017, 13 pages.

Non Final Office Action mailed Aug. 14, 2020 for U.S. Appl. No. 16/810,429, filed Mar. 5, 2020, 20 pages.

Non-Final Office Action mailed Apr. 26, 2021 for U.S. Appl. No. 16/317,235, filed Jan. 11, 2019, 18 pages.

Notice of Allowance for KR Application No. 10-2022-7016510. mailed Mar. 14. 2023, 7 pages.

Office Action for Chinese Application No. 201780054873.2, mailed Sep. 16, 2021, 13 pages.

Office Action for CN Application No. 2022102492594, mailed Dec. 1, 2023, 15 pages.

Office Action for Korean Application No. 1020197004347, mailed Sep. 24, 2021, 9 pages.

Office Action for KR Application No. 10-2022-7016510, mailed Dec. 21, 2022, 9 pages.

Office Action for U.S. Appl. No. 17/529,967, mailed Aug. 4, 2023, 30 pages.

Office Action mailed Nov. 21, 2018 for U.S. Appl. No. 15/903,139, filed Feb. 23, 2018, 10 pages.

Office Action mailed Feb. 3, 2021 for Chinese Application No. 201780054873.2 filed Jun. 22, 2017, 14 pages.

Partial Supplementary European Search Report for Application No. EP17828154.9 mailed on Feb. 4, 2020, 11 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

Extended European Search Report for Application No. EP24185507.1, mailed on Oct. 2, 2024, 08 pages.

\* cited by examiner

MULTI-CABLE MEDICAL INSTRUMENT

CROSS-REFERENCE TO RELATED APPLICATIONS

This patent application is a continuation of U.S. patent application Ser. No. 17/529,967 (filed Nov. 18, 2021), entitled "MULTI-CABLE MEDICAL INSTRUMENT," which is a continuation of U.S. patent application Ser. No. 16/317,235 (filed Jan. 11, 2019), now U.S. Pat. No. 11,207,145, entitled "MULTI-CABLE MEDICAL INSTRUMENT," which is a U.S. national stage filing under 35 U.S.C. § 371 of International Application No. PCT/US2017/038674 (filed Jun. 22, 2017), entitled "MULTI-CABLE MEDICAL INSTRUMENT," which claims priority to and the filing date benefit of U.S. Provisional Patent Application No. 62/362,431 (filed Jul. 14, 2016), entitled "MULTI-CABLE MEDICAL INSTRUMENT," each of which is incorporated herein by reference in its entirety.

BACKGROUND

Robotically controlled instruments such as employed for minimally invasive medical procedures often employ a tool or end effector or other manipulation element at the distal end of an extended instrument shaft. (As used herein, the terms "robot" or "robotically" and the like include teleoperation or telerobotic aspects.) The instrument shaft and the distal tool generally have small diameters, often less than a centimeter, to minimize the size of incisions or natural lumens needed for insertion of the instrument. Accordingly, the distal tools are often remotely operated or actuated via thin drive members (e.g., tendons or rods) that extend between the distal tool and a transmission, sometimes referred to as the backend mechanism of the instrument. The backend mechanism of a replaceable instrument is generally configured to removably couple to actuators (e.g., a motor pack) in a docking port of a robot. The robot can then control the actuators and apply force through the backend mechanism to the drive members and through the drive members to the distal tool of the instrument.

Medical instruments that have many degrees of freedom of movement typically require many drive members, and backend mechanisms that accommodate the transition from the layout of a docking port of a robot to the layout of the drive members in the instrument shaft can be complex and difficult to assemble.

SUMMARY

In accordance with an aspect of the invention, a medical instrument may provide efficient routing of actuation cables and relatively simple assembly process for complex medical instruments.

One specific implementation provides a medical instrument including a chassis, input spindles mounted in the chassis, upper and lower cables wound around the input spindles, and an instrument shaft extending from the chassis and including a mechanical structure providing multiple degrees of freedom of motion. The upper and lower cables may connect to the mechanical structure so that rotations of the input spindles actuate respective degrees of freedom. Lower pulleys may be mounted at a first level to receive the lower cables from the input spindles and to redirect the lower cables toward the instrument shaft. Upper pulleys may be mounted at a second level to receive the upper cables from the input spindles and redirect the upper cables through the first level and toward the instrument shaft.

Another specific implementation is a method for assembling a medical instrument. The method may include: mounting lower pulleys on a first piece of a chassis of the medical instrument; feeding lower cables from an instrument shaft of the medical instrument over the lower pulleys; attaching a second piece of the chassis to the first piece so that at least portions of the lower cables are between the lower pulleys and the second piece; mounting upper pulleys in positions such that the second piece is between the upper pulleys and the lower pulleys; and feeding upper cables from the instrument shaft over the upper pulleys.

Yet another specific implementation is a medical instrument including input spindles, lower cables respectively wound around the input spindles, upper cables respectively wound around the input spindles, and an instrument shaft extending from a chassis in which the input spindles are mounted. A mechanical structure on the instrument shaft has multiple degrees of freedom of motion, and the upper and lower cables connect to the structure such that rotations the input spindles respectively actuate the degrees of freedom. The lower or upper cables may extend between the input spindles and the instrument shaft without crossing, and paths of the other upper or lower cables cross between the input spindles and the instrument shaft. The crossing in one set of cables may allow the upper cable and the lower cable that wrap around the same input spindle to be more efficiently directed toward locations on opposite sides of a central axis of the instrument shaft, which may improve mechanical efficiency of actuation of the mechanical structure.

BRIEF DESCRIPTION OF THE DRAWINGS

The drawings illustrate examples for the purpose of explanation and are not of the invention itself. Use of the same reference symbols in different figures indicates similar or identical items.

DETAILED DESCRIPTION

A backend mechanism of a robotically controlled medical instrument routes cables from multiple input spindles to an instrument shaft of the instrument and employs a routing that allows simple assembly using few components. Cables and associated pulleys in an instrument may be particularly grouped by level or height relative to the instrument shaft, and lower cables may be fit on pulleys mounted in a lower chassis piece before a next, higher chassis piece and pulleys for upper cables are attached to the lower chassis piece. A two-level system is particularly effective in a self-antagonistic system in which each input spindle has a pair of two associated cables that are wrapped around the input spindle in opposite directions and at different heights so that one cable pays in in one direction and the other cable pays out in an opposite direction as the spindle rotates. The cable routing leaves space for other components of the backend of a medical instrument, for example, to allow control or actuation of instrument shaft roll, grip drive, electrical connectors, and latching mechanisms that attach the backend mechanism to a robot. The cable routing can also position cables paired in opposition in the instrument shaft, so that the paired cables can efficiently actuate opposite directions of motion of a degree of freedom of the instrument.

Figure 1:
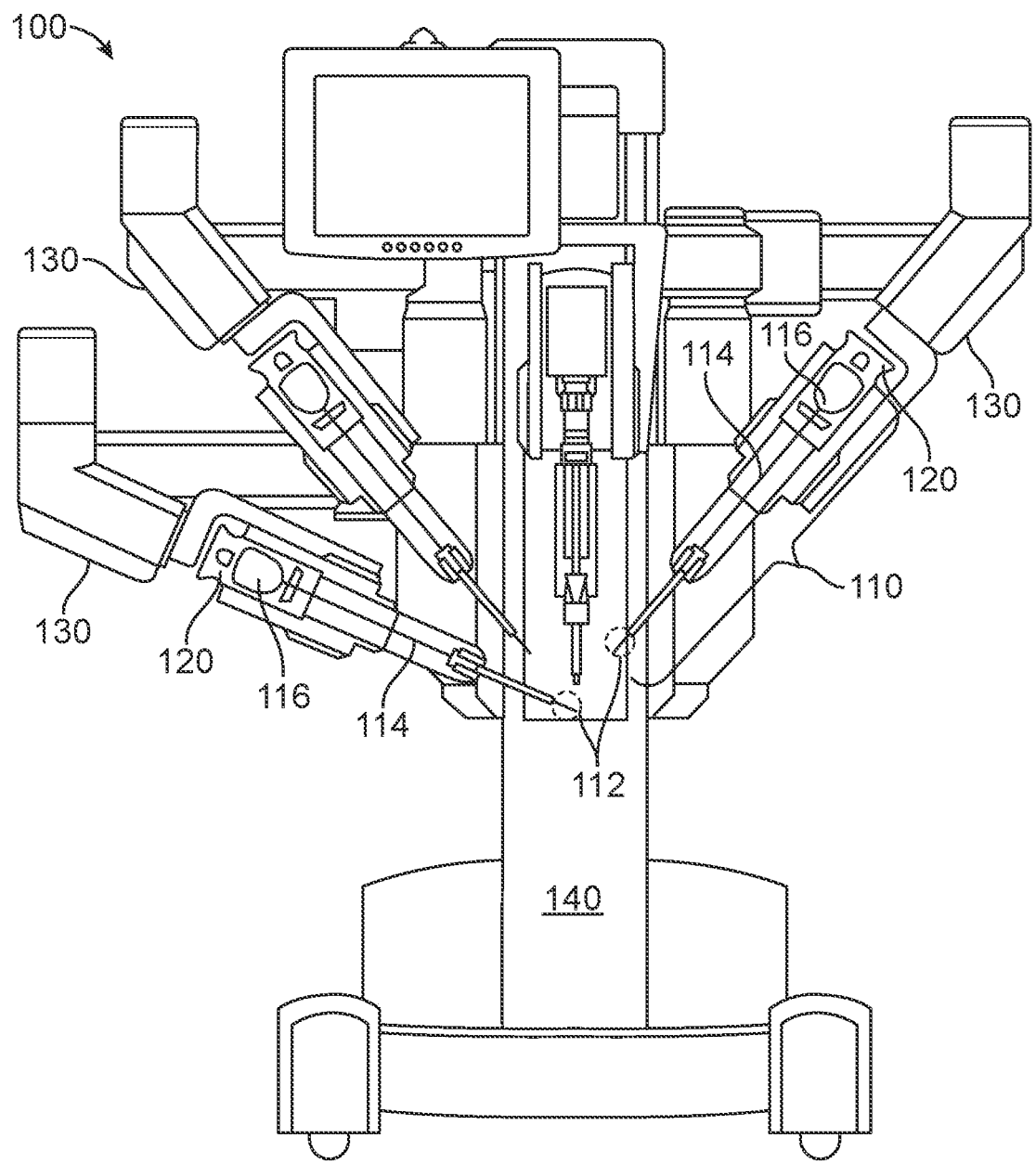
FIG. 1 shows an implementation of a medical system employing removable instruments.

FIG. 1 shows an example of a medical system 100 using replaceable medical instruments 110. System 100, which may, for example, be a da Vinci® Surgical System commercialized by Intuitive Surgical, Inc., may particularly employ multiple surgical instruments 110, each of which is removably mounted in a docking port 120 on a manipulator arm 130 of a robot 140. A sterile barrier (not shown) including a drape and adaptors for instruments 110 may be between instruments 110 and robot 140, so that robot 140, including manipulator arms 130 and docking ports 120, is outside a sterile environment for a patient. Accordingly, robot 140 may not need to be sterilized between medical procedures. In contrast, instruments 110, which may be used in the sterile environment and may contact the patient, are compact and removable so that instruments 110 may be sterilized or replaced between medical procedures performed using system 100.

Instruments 110 may vary in structure and purpose but may still be interchangeable, so that instruments 110 mounted in docking ports 120 of robot 140 can be selected for a particular medical procedure or changed during a medical procedure to provide the clinical functions needed. Each instrument 110 generally includes an end effector or distal tool 112, an instrument shaft 114, and a backend mechanism 116. Distal tools 112 may have different designs to implement many different functions. For example, distal tools 112 for different instruments 110 may have many different shapes or sizes and may include forceps, graspers, scalpels, scissors, cautery tools, or needle drivers to name a few possibilities, and instruments 110 having different distal tools 112 may be mounted on different arms 130 of robot 140 and may work cooperatively in the same work site. An endoscopic camera, for example, a stereoscopic camera, can also be mounted on an arm to provide visual information, particularly images, of the work site in which distal tools 112 of instruments 110 may be operating.

Docking ports 120 may include actuators, such as drive motors, that provide mechanical power for actuation of mechanical structures in instruments 110, drive couplings that connect the actuators to inputs of instruments 110, and systems for establishing and maintaining a sterile barrier between instruments 110 and the rest of medical system 100. Docking ports 120 may additionally include an electrical interface to provide power to instruments 110 or for communication with instruments 110, for example, to identify the type of instrument 110 in a docking port 120, to access parameters of instruments 110, or to receive information from sensors in instruments 110. For example, the electrical interface may convey to robot 140 measurements such as measurements of the position, orientation, or pose of distal tool 112 and instrument shaft 114 of an instrument 110. A computer system, which may be connected to or part of robot 140 and connected to a user interface device (not shown), may receive the measurements from instrument 110 and receive user commands from a surgeon or other medical personnel and may execute software that controls arms 130 and drive motors in docking ports 120 as needed to operate instruments 110 according to the user commands.

Figure 2A:
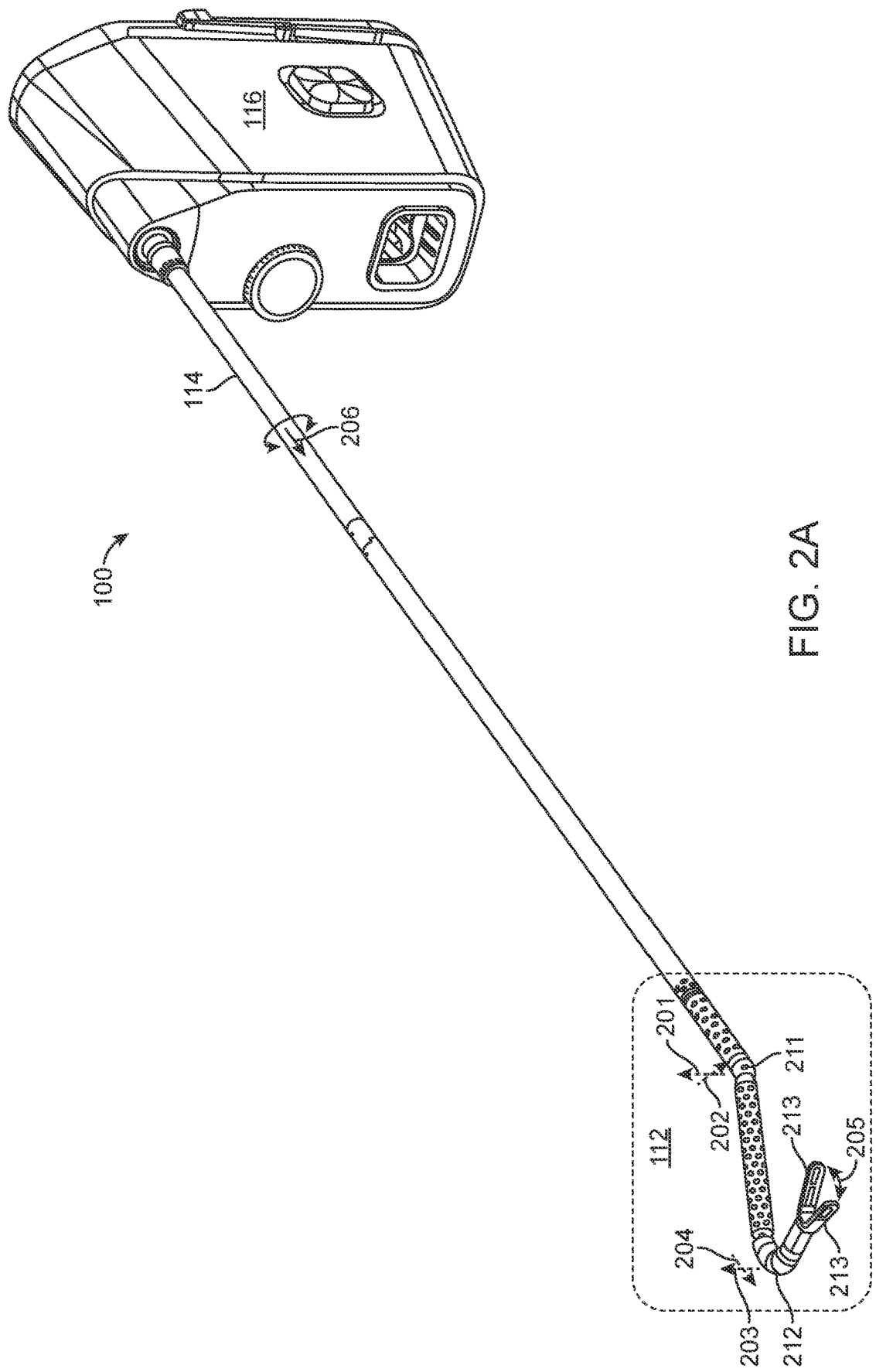
FIGS. 2A and 2B show side and top views of an example implementation of a medical instrument.
Figure 2B:
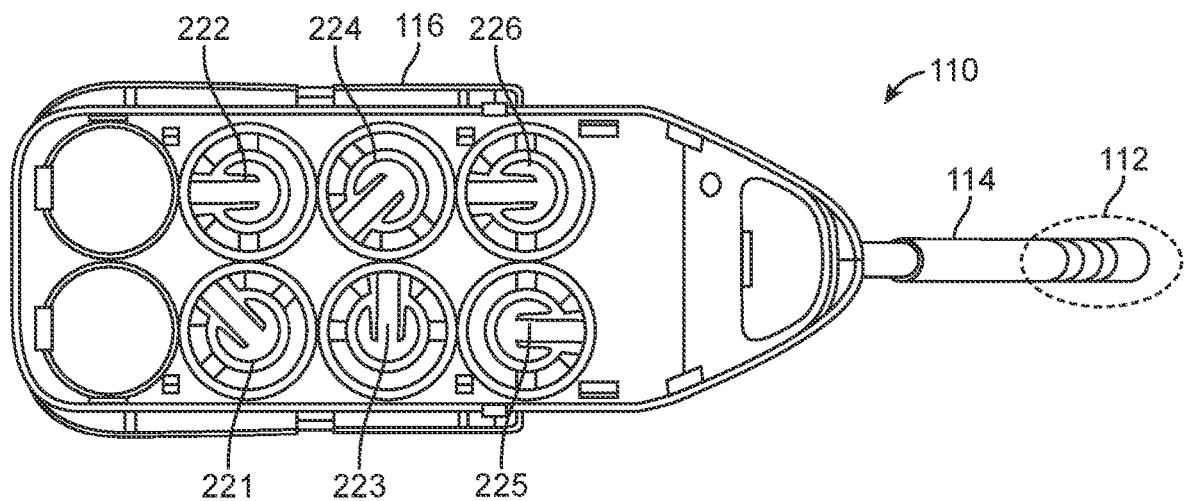

FIGS. 2A and 2B illustrate an example implementation of a medical instrument 110. FIG. 2A particularly shows a perspective view of an implementation having a tool 112 at the distal end of instrument shaft 114 and shows instrument shaft 114 extending from backend mechanism 116. In the illustrated implementation, distal tool 112 and instrument shaft 114 have six degrees of freedom of movement relative to backend mechanism 116. In particular, the six degrees of freedom correspond to: pitch and yaw rotations of a distal portion of tool 112 about two respective perpendicular axes 201 and 202 associated with a first joint mechanism 211 (also called "first joint 211"); pitch and yaw rotations or movement of jaws 213 relative to two respective perpendicular axes 203 and 204 associated with a second joint mechanism 212 (also called "second joint 212"; the joints 211, 212 are sometimes referred to as "wrists"); opening or closing movement 205 of jaws 213 for "grip" actuation; and "roll" rotations of instrument shaft 114 about its central length axis 206. Other instruments may have more, fewer, or different degrees of freedom of movement.

Backend mechanism 116 as shown in FIG. 2B has six input spindles 221 to 226 with engagement features that are shaped and positioned to engage actuators, e.g., drive motors, in a docking port of a robot. In general, each input spindle 221 to 226 may be coupled for actuation of a different degree of freedom of movement of the instrument, so that the robot can identify and use the correct actuator or actuators to rotate the spindle or spindles that exercise desired degrees of freedom of motion. The assignment input spindles 221 to 226 to corresponding degrees of freedom must be known to the robot but can be otherwise defined by an arbitrary standard or convention. In an exemplary implementation, input spindle 226 may couple to a roll mechanism that connects to a proximal end of instrument shaft 114 for rotation of instrument shaft 114 about its length axis 206 when input spindle 226 rotates. Input spindles 221 to 225 may couple to drive members (not shown) such as cables or rods extending though instrument shaft 114 to distal tool 112, so that the actuators in the robot can rotate input spindles 221 to 225 to control a distal mechanism including joints 211 and 212 and jaws 213. More specifically, in an exemplary implementation, rotation of input spindle 221 may control rotation or actuation of a distal portion of tool 112 about an axis 201. Rotation of input spindle 222 may control rotation about an axis 202. Rotation of input spindle 223 may control rotation about an axis 203 for yaw actuation of jaws 213, and rotation of input spindle 224 may control rotation about an axis 204 for pitch actuation of jaws 213. In some implementations, rotations of input spindles 221 to 226 may correspond to motion that is different from or more complex than simple rotations of structures about axes. For example, input spindle 225 may be coupled to jaws 213 through a push-pull rod for actuation of gripping with jaws 213. Also, in a particular implementation, the mechanism in tool 112 may couple a proximal portion of joint 212 to a distal portion of joint 211 for parallelogram motion, while the distal portion of joint 212 may move independently.

Figure 3:
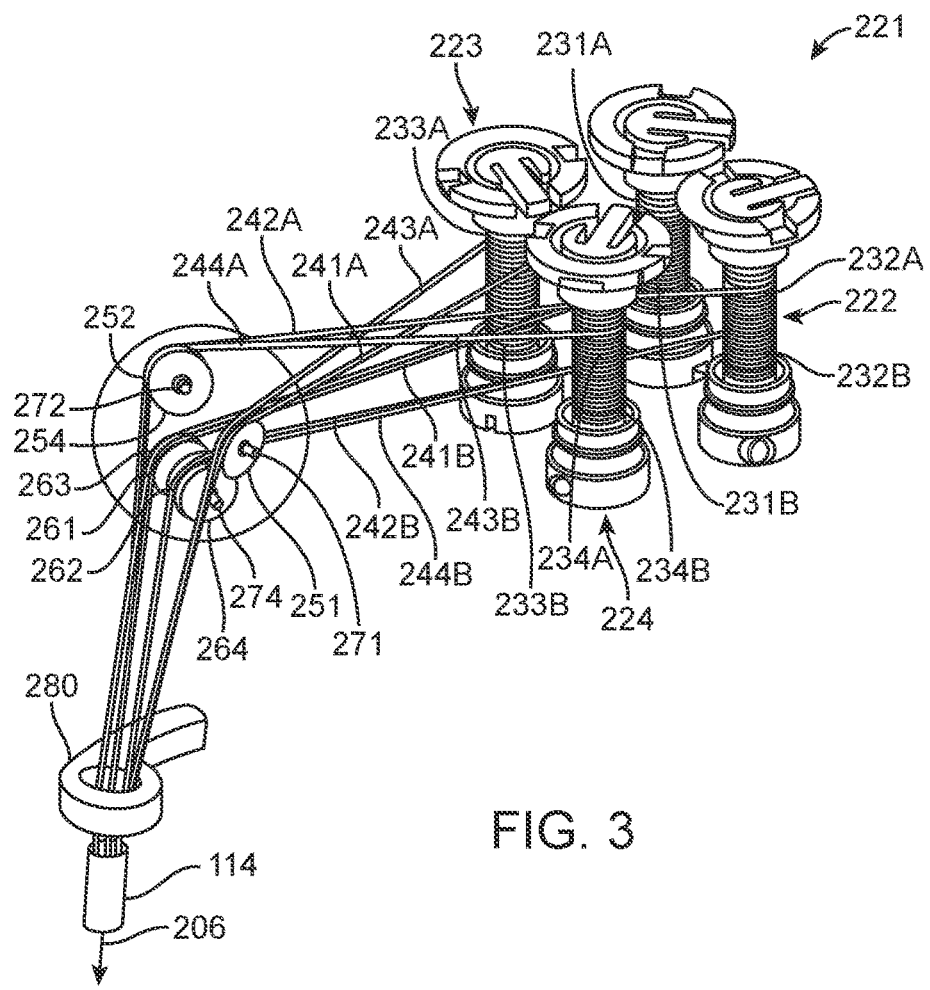
FIG. 3 shows cable routing in an example implementation of a backend mechanism of a medical instrument.

FIG. 3 shows selected elements within an implementation of the backend mechanism 116 of FIGS. 2A and 2B and particularly illustrates a routing in backend mechanism 116 of cables that run through instrument shaft 114 and connect to joints 211 and 212. The term "cable" is used herein in a broad sense to include any tendon-like structure. In particular, a length of cable in a medical instrument may include sections of different materials or different characteristics. A cable may include, for example, a stranded section where flexibility in the cable is desired (e.g., where the cable winds around a spindle, capstan, or pulley) and may include a more rigid section (e.g., a tube or rod) to limit stretching where less bending of the cable is needed. FIG. 3 does not show elements of backend mechanisms 116 that may be used for actuation of degrees of freedom associated with rotation of instrument shaft 114 or for opening and closing of jaws 213. Co-filed U.S. Pat. App. No. 62/362,340 (filed Jul. 14, 2016), entitled "GEARED ROLL DRIVE FOR MEDICAL INSTRUMENT", and U.S. Pat. App. No. 62/362,365 (filed Jul. 14, 2016), entitled "GEARED GRIP ACTUATION FOR MEDICAL INSTRUMENTS", disclose aspects of particular implementations of such mechanisms and are hereby incorporated by reference in their entirety.

Input spindles 221, 222, 223, and 224, as described above, are for actuation of degrees of freedom associated with respective axes 201, 202, 203, and 204, and each input spindles 221, 222, 223, and 224 includes a pair of capstans around which a pair of actuation cables are wrapped. For example, as shown in FIG. 3, an upper capstan 231A and a lower capstan 231B may be fixed on an axle of input spindle 221 so that both capstans 231A and 231B rotate with rotation of input spindle 221. (The terms upper and lower are used here to distinguish levels and may only apply literally when instrument shaft 114 points in a generally downward direction, as illustrated in FIG. 3.) A cable 241A wraps in one direction (e.g., clockwise or counterclockwise) around capstan 231A, and a cable 241B wraps in the opposite direction (e.g., counterclockwise or clockwise) around capstan 231B. Cable 241A extends from upper capstan 231A to an upper pulley 251 that directs cable 241A toward instrument shaft 114. Similarly, cable 241B extends from lower capstan 231B to a lower pulley 261 that directs cable 241B toward instrument shaft 114. Cables 241A and 241B extend from respective pulleys 251 and 261 through a guide 280, into instrument shaft 114, and through instrument shaft 114 to connect to actuated joint mechanism 211, so that pulling cable 241A or 242B rotates a distal portion of mechanism 211 (and distal portions of tool 112) about axis 201. The positions of pulleys 251 and 261 and the shape of guide 280 may position cables 241A and 241B on opposite sides of the center or length axis 206 of instrument shaft 114, which may allow cable 241A to efficiently drive motion of mechanism 211 in one direction or sense about axis 201 and also allow cable 241B to efficiently drive motion of mechanism 211 in an opposite direction or sense about axis 201.

Each input spindle 222, 223, or 224 similarly includes an axle through a pair of capstans 232A and 232B, 233A and 233B, or 234A and 234B around which a pair of cables 242A and 242B, 243A and 243B, or 244A and 244B wrap in opposite directions, and cables 242A, 242B, 243A, 243B, 244A, and 244B pass over respective pulleys 252, 262, 253, 263, 254, and 264 and run through guide 280 and instrument shaft 114. In an exemplary implementation, cables 242A and 242B connect to joint mechanism 211, and cables 243A, 243B, 244A, and 244B connect to joint mechanism 212.

Each pair of cables 242A and 242B, 243A and 243B, and 244A and 244B as described above includes one cable wound in one direction (e.g., clockwise) about an input spindle 221, 222, 223, or 224 and another cable wound in the other direction (e.g., counterclockwise) around the input spindle 221, 222, 223, or 224, so that rotation of an input spindle 221, 222, 223, or 224 pulls in one cable while paying out another cable. Accordingly, instrument 110 may employ self-antagonistic actuation in which each pair of cables 241A and 241B, 242A and 242B, 243A and 243B, or 244A and 244B controls a corresponding degree of freedom of movement, e.g., rotations about axes 201, 202, 203, or 204, of the instrument. Non-antagonistic cable actuation may be used in some embodiments (e.g., one cable per spindle).

In the illustrated system, mechanisms 211 and 212 are wrists or joints that each provide two degrees of freedom of movement. Many other mechanisms can provide one or more degrees of freedom of movement and may be connected so that one or more pairs of cables can respectively actuate the one or more degrees of freedom. An actuated mechanism may, for example, include a mechanical linkage with a link that is rotatable about a pivot, and a pair of cables may be connected to rotate the link in opposite directions relative to the pivot. Alternatively, actuated mechanisms may be any structure, e.g., a linkage, a slide, or a flexure, capable of being moved/actuated in opposite directions. For each pair of cables, pulling one cable may drive actuation of the corresponding degree of freedom in one direction or sense, and pulling the other cable in the pair may drive actuation of the corresponding degree of freedom in an opposite direction or sense.

Routing of cables 241A, 242A, 243A, and 244A employs upper pulleys 251, 252, 253, and 254 to receive cables 241A, 242A, 243A, and 244A from upper capstans 231A, 232A, 233A, and 234A and employs lower pulleys 261, 262, 263, and 264 to receive cables 241B, 242B, 243B, and 244B from respective lower capstans 231B, 232B, 233B, and 234B. Upper pulleys 251, 252, 253, and 254 may all be positioned at about the same common height, while lower pulleys 261, 262, 263, and 264 may all be positioned at about another common height that differs from the common height of upper pulleys 251, 252, 253, and 254. This allows the pulleys to be captured in stacked blocks or chassis pieces as described further below.

The arrangement of upper pulleys 251, 252, 253, and 254 and lower pulleys 261, 262, 263, and 264 may also be simplified by pairing pulleys to independently spin on shared axles. Using pulleys that share an axle may allow faster assembly, because multiple pulleys can be added to a structure by attaching a single axle. In the implementation of FIG. 3, input spindles 221, 222, 223 and 224 are arranged in a rectangular array, e.g., in rows and columns, and paths of cables from input spindles in the same row to locations over instrument shaft 114 are roughly parallel. Accordingly, pulleys 251 and 253, which guide cables 241A and 243A running at the same height and substantially the same direction from input spindles 221 and 223, can be mounted on a common axle 271. Similarly, upper pulleys 252 and 254, which guide cables 242A and 244A that emerge from input spindles 222 and 224 with substantially the same height and direction, can be mounted on a shared axle 272. Lower pulleys 262 and 264, which guide cables 242B and 244B that emerge from input spindles 222 and 224 with substantially the same height and direction, can be mounted on another shared axle (not visible in FIG. 3), and lower pulleys 261 and 263, which guide cables 241B and 243B that emerge from input spindles 222 and 224 with substantially the same path and direction can be mounted on yet another shared axle 274.

Pulley axles 271 to 274 may also be angled according to exit directions of the cables from the input spindles 221 to 224 and relative to the central axis 206 of instrument shaft 114. For example, axle 271 may be turned about a first axis (e.g., an axis parallel to the axles of input spindles 221 to 224) to minimize the fleet angles at pulleys 251 and 253 of cables 241A and 243A from input spindles 221 and 223. Axle 271 may be turned about a second axis (e.g., an axis approximately parallel to the portion of cables 241A and 243A between pulleys 251 and 253 and capstans 231A and 233A) so that the portion of cables 241A and 243A between pulleys 251 and 253 and guide 280 converge toward guide 280 and instrument shaft 114. The angling of axles 271 to 274 may reduce the average fleet angle for entry and exit of the cables from the upper and lower pulleys and thereby reduce friction and wear.

Axles 271 to 274 may further be positioned relative to input spindles 221 to 224 and instrument shaft 114 to minimize wrap angles across sliding surfaces on the pulleys. The positions of the pulleys may be further refined according to the desired cable paths exiting guide 280. In particular, redirection of any cable passing through guide 280 should only cause rubbing on the resilient surface (e.g., a metal portion) of guide 280 and not a softer surface (e.g., a plastic portion) of guide 280. The wrap angle across guide 280 should also be small so that the friction and sawing action any cable against guide 280 is small. The cable path should further be relatively direct so that length of stranded cable does not negatively affect the overall stiffness of the drive train between the corresponding input spindle and the actuated mechanism. In general, the stranded sections of cables tend to stretch more than the rigid hypotube sections used in some embodiments.

The separations between input spindles 221 to 224 may be considerably larger than the diameter of instrument shaft 114 into which the cables need to be directed. Accordingly, the paths of the cables need to converge between input spindles 221 to 225 and instrument shaft 114. The cables also should not rub against each other or against any other structures in backend mechanism 116. To avoid cable interference, the winding directions of cables 241A, 241B, 242A, 242B, 243A, 243B, 244A, and 244B around the input spindles in the illustrated implementation are chosen so that cables at one level (e.g., lower cables 241B, 242B, 243B and 244B) emerge from inside the array of input spindles 221 to 224, and cables at other levels (e.g., upper cables 241A, 242A, 243A and 244A) emerge from an outer edge of the array of input spindles. Lower cables 241B, 242B, 243B and 244B, which emerge from inside an area of the input spindle array, can directly converge at a relatively small angles toward instrument shaft 114 without interfering with each other or rubbing against other structures, such as input spindles 223 or 224. Upper cables 241A, 242A, 243A and 244A, which emerge from the outer edge of input spindles 221 to 224, have crossing paths, which increases the angle of convergence. In particular, upper cables 241A and 243A, which emerge from input spindles 221 and 223, cross over upper cables 242A and 244A, which emerge from input spindles 222 and 224. For the crossing pattern, upper pulleys 251 and 253, which are within the same level group as upper pulleys 252 and 254, although having a generally common height may be staggered in height (e.g., so that cables 241A and 243A can cross over cables 242A and 244A without rubbing). The larger angle of convergence provided by the crossing pattern allows cables 241A and 242A to pass from outer edges of input spindles 221 and 222 through the gap between input spindles 223 and 224. The crossing pattern also allows pulleys 251 and 253, which receive cables 241A and 243A, to be farther from pulleys 252 and 254, which receive cables 242A and 244A, than pulleys 261 and 263 are from pulleys 262 and 264. The wider spacing of upper pulleys 251 to 254 allows routing cables 241A to 244A toward instrument shaft 114 without interference from lower pulleys 261 to 264 or cables 241B to 244B. Crossing one level of cables in this fashion also allows positioning of cables that wrap about the same input spindle and that are therefore paired for actuation of the same degree of freedom in opposition in instrument shaft 114, which may permit efficient connection of the pair of cables to an actuated mechanism.

The cable routing in the implementation of FIG. 3 may provide several advantages. In particular, the difference in the horizontal separation of upper pulleys 251 to 254 from the horizontal separation of lower pulleys 261 to 264, may allow upper pulleys 251 to 254 to be vertically positioned closer to lower pulleys 261 to 264, e.g., at a vertical separation that is less than the diameter of pulleys 251 to 254 and 261 to 264. Also, upper pulleys 251 to 254 and lower pulleys 261 to 264 may be at the same distance from the closest input spindles 223 and 224. Since one group of pulleys is not required to be closer to the input spindles, all of the pulleys can be at a relatively long distance from the input spindles, which may minimize the splay angles for the actuation cables. A crossing cable pattern may further reduce the space needed to accommodate the required splay. The cable routing can position pulleys so that the cables do not rub on each other or on neighboring input spindles and do not require additional intermediary idler pulleys.

Figure 4:
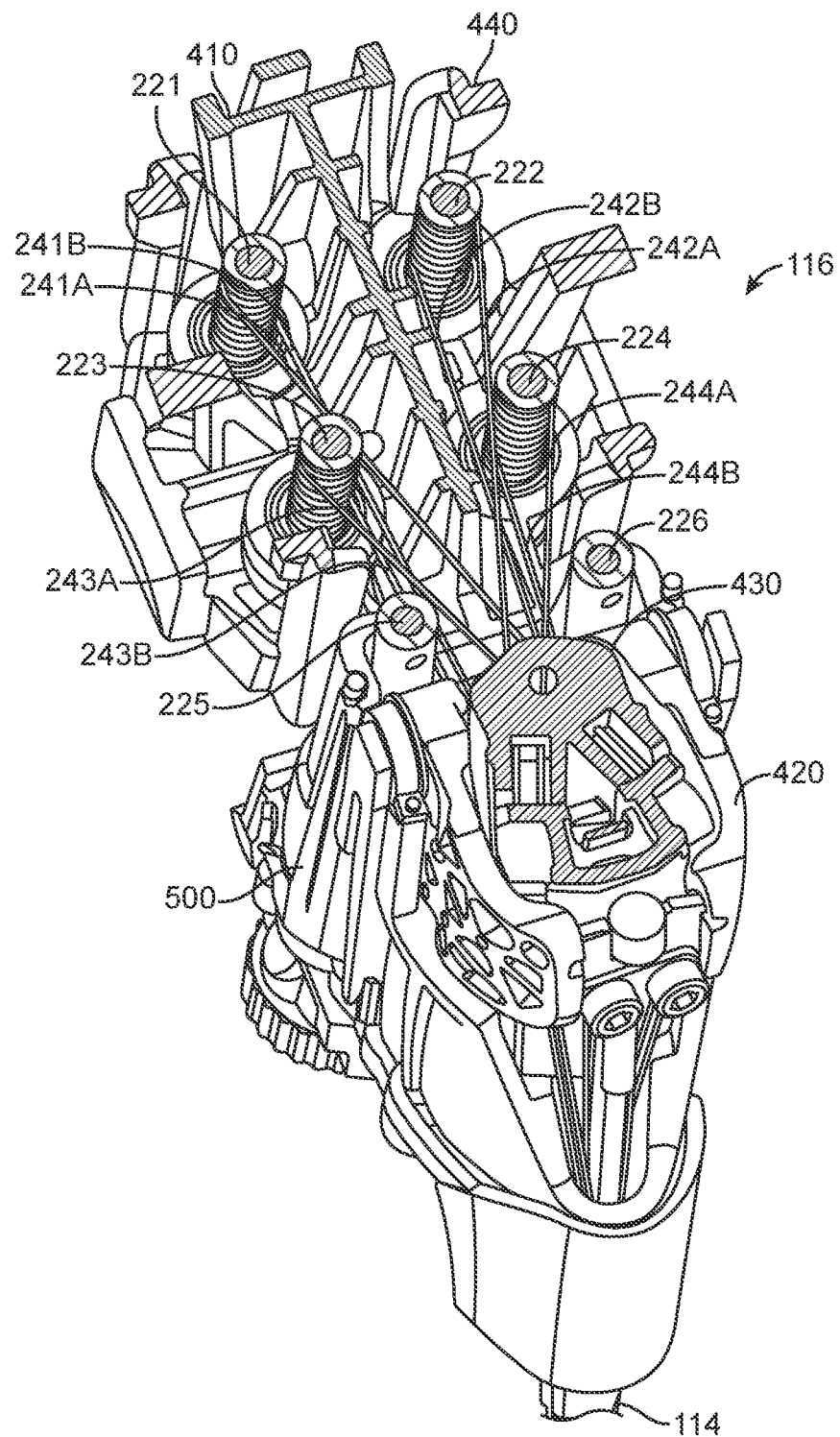
FIG. 4 is a cross-sectional view illustrating a routing of cables relative to a chassis and other structures in an example implementation of a backend mechanism of a medical instrument.

FIG. 4 shows a cross-sectional view of internal structure in an example implementation of a backend mechanism 116. As illustrated, backend mechanism 116 may include a chassis 500 with a central support structure 410 that extends between rows of input spindles 221, 222, 223, and 224. The routing of cables 241A to 244A or 241B to 244B allows use of central support structure 410 to strengthen chassis 500 without interfering with cables 241A to 244A or 241B to 244B. The cable routing also causes cables 241A to 244A or 241B to 244B to converge sufficiently to pass between input spindles 225 and 226, through an opening in a linkage 420 for actuation of jaws 213, and through an opening in a linkage 430 used for actuation of rotation about instrument shaft axis 206. This configuration with support structure 410 in the center of backend mechanism 116 opens up access to input spindles 221, 222, 223, and 224 from around the perimeter of chassis 500, for example, to attach and wrap cables 241A to 244A or 241B to 244B on capstans 231A to 234A and 231B to 234B and to tighten capstan clamping screws during assembly of backend mechanism 116. Once input spindles 221, 222, 223, and 224 are mounted in chassis 500 and capstans 231A to 234A and 231B to 234B are wrapped and clamped, the space around input spindles 221, 222, 223, and 224 is available for other structures, such as a structure 440, for latching backend mechanism to a docking port on a robot.

Figure 5:
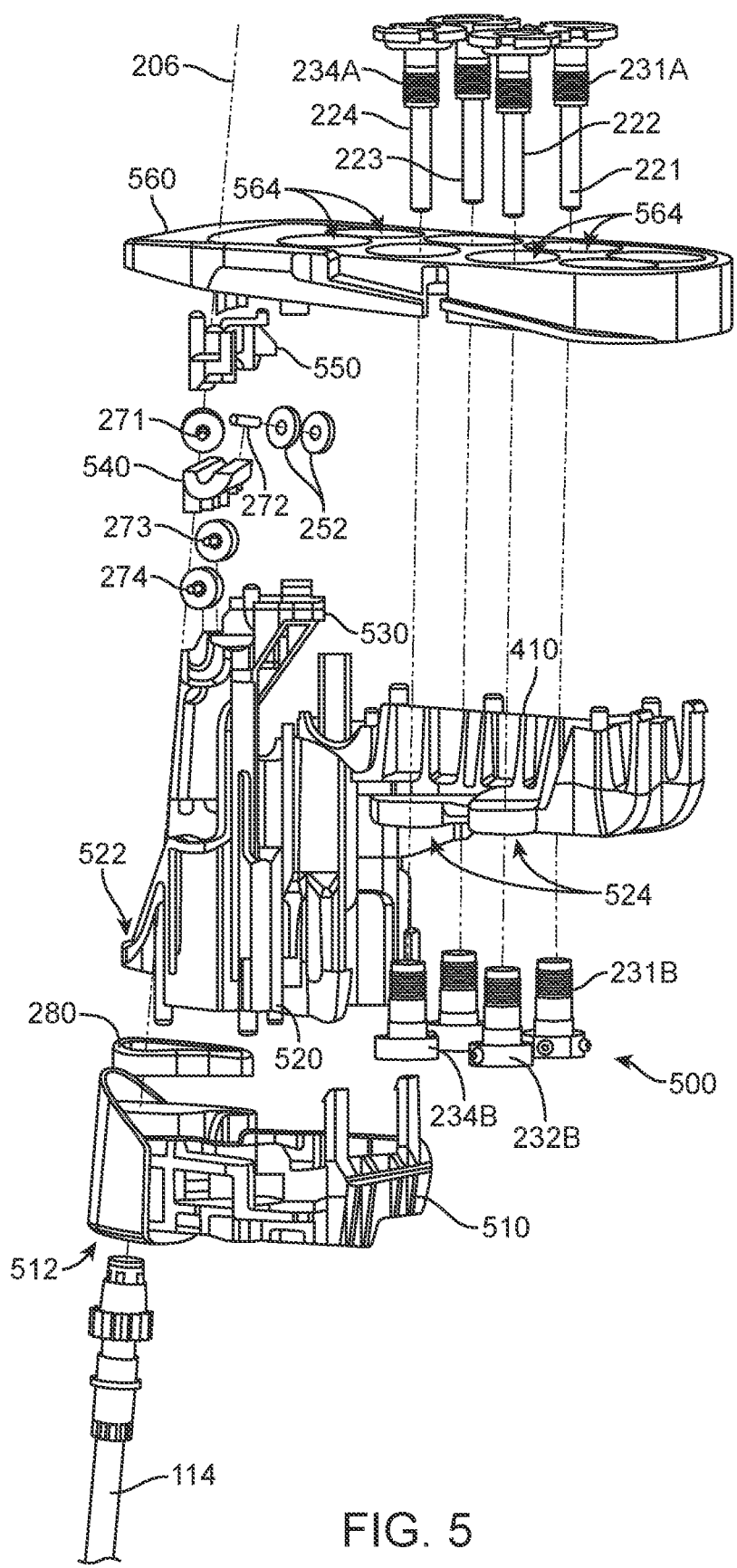
FIG. 5 is an expanded view of an implementation of a medical instrument including a backend mechanism with a multi-piece chassis.

FIG. 5 shows an expanded view of some of the components in an implementation of a medical instrument with a multi-piece chassis 500 for a backend mechanism 116. Chassis 500 includes pieces 510, 520, 530, 540, 550 and 560 that may be snapped together during an assembly process. During the assembly process, a proximal end of instrument shaft 114 may be inserted in a bearing system in chassis piece 510, at which point cables, e.g., cables 241A to 244A and 241B to 244B, which are attached to the distal tool of the instrument extend from instrument shaft 114. The cables may then be fed through desired locations in guide 280, and chassis piece 520 may be attached to chassis piece 510 so that guide 280 is captured between chassis pieces 510 and 520. All or portions of grip or roll gears or mechanisms that couple to input spindles 225 or 226 may also be assembled on chassis pieces 510 and 520 before chassis pieces 510 and 520 are snapped together and may be held in place by chassis pieces 510 and 520. An upper portion of chassis piece 520 further includes central support structure 410, which is described above and includes features 524 shaped to hold lower capstans 231B to 234B which will be mounted on input spindles 221 to 224.

The assembly process can then connect chassis piece 530 to chassis piece 520. Chassis pieces 530 and 520 are separate to allow for the assembly of linkage 420 that couples to input spindle 525 and is employed for grip actuation in the exemplary implementation.

Figure 6A:
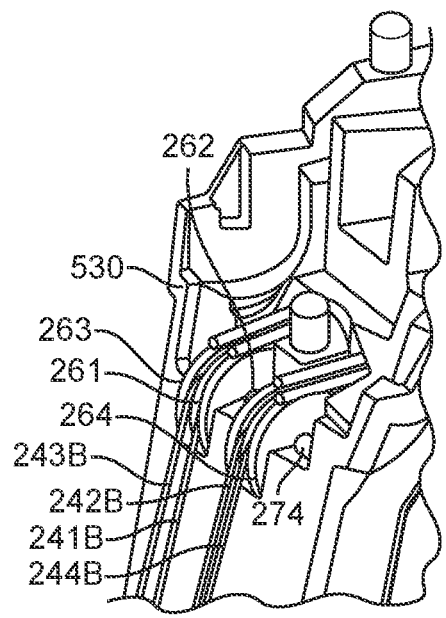
FIGS. 6A, 6B, and 6C illustrate a pulley structure created during an assembly process for a backend mechanism that routes cables between an instrument shaft of a medical instrument and a set of input spindles around which the cables wrap.

Chassis piece 530 has an upper portion shaped to hold axles 273 and 274 for lower pulleys that guide the actuation cables and redirect the actuation cables toward the instrument shaft. As shown in FIG. 6A, lower pulleys 263 and 261 on axle 273 may be mounted in slots formed in chassis piece 530. Similarly, lower pulleys 262 and 264 on axle 274 are mounted in another set of slots in chassis piece 530. Lower cables 241B, 242B, 243B, and 244B, which extend from instrument shaft 114, may be seated in grooves on respective lower pulleys 261, 262, 263, and 264 and threaded through openings in chassis piece 530 so that proximal ends of lower cables 241B, 242B, 243B, and 244B are near features 524 where input spindles 221 to 224 will reside.

Figure 6B:
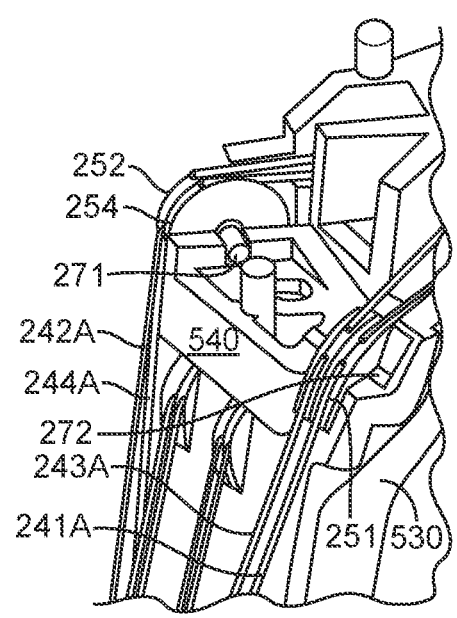
Figure 6C:
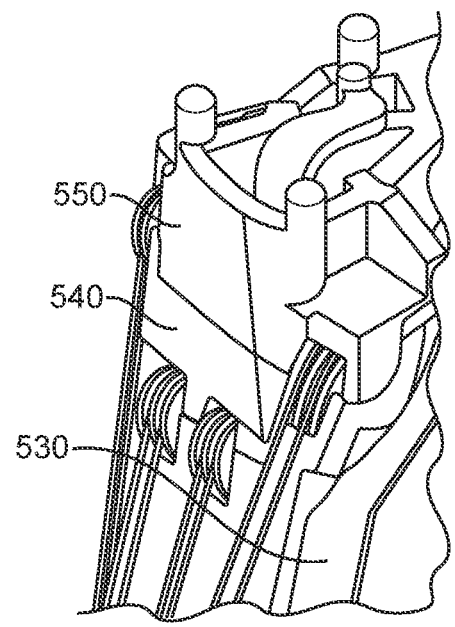
Figure 6D:
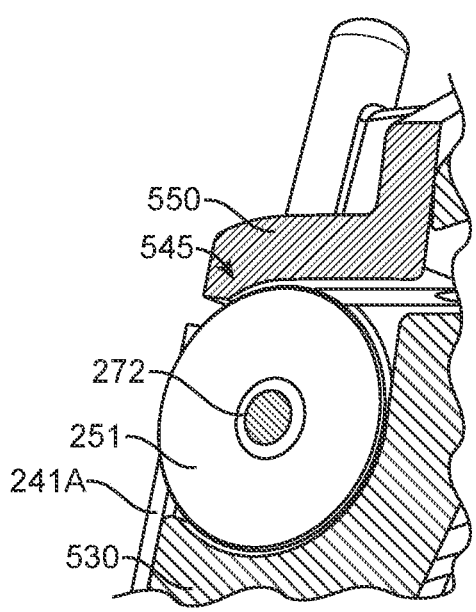
FIG. 6D shows a cross-section of a portion of an example implementation of a backend mechanism and illustrates how pieces of a chassis may be fit close to a pulley to prevent cable derailment.

The assembly process can next connect a chassis piece 540 to chassis piece 530 as shown in FIG. 6B. Chassis piece 530 and 540 may be shaped to provide a close fit between chassis piece 540 and pulleys 261 to 264 so that cables 241B, 242B, 243B, and 244B are not easily derailed. Upper pulleys 251 and 253 on axle 272 and upper pulleys 252 and 254 on axle 271 may be mounted in slots created by the combination of chassis pieces 530 and 540. The slot into which axle 271 fits may be at slightly different level from the slot into which axle 272 fits so that the upper cables can cross as described above. Upper cables 241A, 242A, 243A, and 244A may be seated on respective upper pulleys 251, 252, 253, and 254 and threaded through openings in chassis 500 so that proximal ends of upper cables 241A, 242A, 243A, and 244A are also near features 524. A chassis piece 550 connects to chassis pieces 530 and 540 as shown in FIG. 6C and may be shaped to provide a close fit to upper pulleys 251 to 254 so that upper cables 241A, 242A, 243A, and 244A are not easily derailed. FIG. 6D particularly shows a cross-sectional view illustrating how chassis piece 550 when mounted on pieces 530 and 540 may be close fit to pulley 251 so that a gap 545 between chassis piece 550 and pulley 251 is narrower than the thickness of cable 241A on pulley 251. As a result, cable 241A fits into the grove in pulley 251 and cannot slip through gap 545.

Returning to FIG. 5, a chassis piece 560 snaps onto or otherwise connects to one or more of chassis pieces 520, 530, and 550. The top of chassis piece 560 is shaped to fit a docking port of a robot and includes features 564 that are shaped and located to hold the engagement features of input spindles 221 to 224 of the instrument. When chassis piece 560 attaches to the assembly including pieces 510, 520, 530, 540, and 550, chassis 500 may capture input spindles 221 to 224 between features 564 on chassis piece 560 and features 524 on chassis piece 520. Each input spindle may include an axle and a pair of capstans, e.g., upper capstans 231A to 234A and lower capstans 231B to 234B, which are initially free to rotate relative to each other. The loose proximal ends of the actuation cables near features 524 may be attached to the corresponding one of capstans 231A to 234A or 231B to 234B. Each capstan can then be independently rotated to wind the attached cable in the desired direction and to take up slack and provide a desired pre-tension in the attached cable. Once both cables wrapped around an input spindle have the desired cable tensioning, the capstans can be clamped or locked in place on the axle of the input spindle, e.g., by tightening a clamping screw. Other structures such as release levers comprising structure 440 of FIG. 4 may wrap around the outside of the actuation structure and cables and may be installed after assembly of the input spindles and routing of cables. Co-filed U.S. Pat. App. No. 62/362,454 (filed Jul. 14, 2016), entitled "INSTRUMENT RELEASE", describes structures such as release levers comprising structure 440 in more detail and is hereby incorporated by reference in its entirety.

The instrument assembly and cable routing process illustrated by FIGS. 5 and 6A to 6D may be relatively simple when compared to the complexity of the instrument. In particular, achieving the desired cable routing does not require simultaneous threading of cables through and around a complex sequence of structures from which the cables may slip. Instead, assembly can proceed in a series of simple steps with the cables being in a secure configuration after each step. Further, the shape of the chassis provides good access to input spindles for cable connections.

Although particular implementations have been disclosed, these implementations are only examples and should not be taken as limitations. Various adaptations and combinations of features of the implementations disclosed are within the scope of the following claims. For example, although embodiments that employ rotating spindles have been described, other means of controlling cable motion may be used. These means include, for example, sliding tabs, levers, gimbals, and the like.

What is claimed is:

1. A medical instrument, comprising:
   a chassis;
   a plurality of input spindles including a first input spindle and a second input spindle each mounted to the chassis;
   a plurality of cables including a first cable, a second cable, a third cable, and a fourth cable;
   the first cable and the second cable each coupled to the first input spindle;
   the third cable and the fourth cable each coupled to the second input spindle;
   an instrument shaft having a first end and a second end, the first end of the instrument shaft coupled to the chassis;
   a tool coupled to the second end of the instrument shaft, the plurality of cables coupled to the tool such that rotations of one or more input spindle from the plurality of input spindles actuate the tool;
   a plurality of first pulleys mounted at a first level on the chassis; and
   a plurality of second pulleys mounted at a second level on the chassis,
   the first cable and the third cable each extend between the plurality of input spindles and the plurality of first pulleys without crossing each other; and the second cable and the fourth cable each extend between the plurality of input spindles and the plurality of second pulleys such that the second cable crosses the fourth cable.

2. The medical instrument of claim 1, wherein:
the chassis includes a first piece on which the plurality of first pulleys is mounted, and
a second piece mounted over the first piece so that the plurality of first pulleys is located between the first piece and the second piece.

3. The medical instrument of claim 1, wherein:
the second cable is directed toward a location on a first side of a central axis of the instrument shaft and the fourth cable is directed toward a location opposite the first side of the central axis of the instrument shaft.

4. The medical instrument of claim 1, wherein:
the first cable wraps around the first input spindle in a first direction, and the second cable wraps around the first input spindle in a second direction opposite the first direction.

5. The medical instrument of claim 1, further comprising:
the first plurality of pulleys is positioned to rotate about a first axis, at least one pulley from the second plurality of pulleys is positioned to rotate about a second axis, and the first axis is nonparallel to the second axis.

6. The medical instrument of claim 1, wherein:
a first pulley from the first plurality of pulleys is spaced from a second pulley from the second plurality of pulleys such that a vertical separation between the first pulley of the first plurality of pulleys and the second pulley from the second plurality of pulleys is less than a diameter of the first pulley and less than a diameter of the second pulley.

7. The medical instrument of claim 6, wherein:
the first pulley is positioned to rotate about a first axis, the second pulley is positioned to rotate about a second axis, and the first axis is nonparallel to the second axis.

8. The medical instrument of claim 6, wherein:
the first pulley redirects the first cable into and through the instrument shaft, and
the second pulley redirects the second cable through the first level and into and through the instrument shaft.

9. A medical instrument, comprising:
a chassis;
a first input spindle mounted to the chassis;
a second input spindle mounted to the chassis;
a support structure extending between the first input spindle and the second input spindle such that the first input spindle is positioned on a first side of a central axis of the chassis and the second input spindle is positioned on a second side of the central axis opposite the first side with the support structure therebetween, the support structure providing strength to the chassis;
a first cable coupled to the first input spindle;
a second cable coupled to the second input spindle;
an instrument shaft having a first end and a second end, the first end of the instrument shaft coupled to the chassis;
a tool coupled to the second end of the instrument shaft, the first cable and the second cable coupled to the tool such that rotations of at least one or more of the first input spindle or the second input spindle actuates the tool;
a first pulley mounted at a first level on the chassis; and
a second pulley mounted at a second level on the chassis different from the first level,
the first cable routed from the first input spindle to the first pulley and into the instrument shaft, and
the second cable routed from the first input spindle to the second pulley and into the instrument shaft.

10. The medical instrument of claim 9, wherein:
the second cable is routed from the second input spindle, through the first level, and into and through the instrument shaft.

11. The medical instrument of claim 9, further comprising:
a linkage coupled to the chassis;
a third input spindle positioned between the first input spindle and the linkage; and
a fourth input spindle positioned between the second input spindle and the linkage,
the first cable being routed from the first input spindle, between the third input spindle and the fourth input spindle, through an opening in the linkage, to the first pulley and into and through the instrument shaft, and
the second cable being routed from the second input spindle, between the third input spindle and the fourth input spindle, through the opening in the linkage, to the second pulley and into and through the instrument shaft.

12. The medical instrument of claim 9, wherein:
the chassis includes a first piece on which the first pulley is mounted, and
a second piece mounted over the first piece so that the first pulley is located between the first piece and the second piece.

13. The medical instrument of claim 9, wherein:
the first pulley is spaced from the second pulley such that a vertical separation between the first pulley and the second pulley is less than a diameter of the first pulley and less than a diameter of the second pulley.

14. The medical instrument of claim 9, further comprising:
a plurality of first cables including the first cable;
a plurality of second cables including the second cable;
a plurality of first pulleys mounted at the first level on the chassis, the plurality of first pulleys including the first pulley; and
a plurality of second pulleys mounted at the second level on the chassis, the plurality of second pulleys including the second pulley.

15. The medical instrument of claim 14, wherein:
the plurality of first cables includes a third cable, the first cable and the third cable each extend between the first input spindle and the first pulley without crossing each other; and
the plurality of second cables includes a fourth cable, the second cable and the fourth cable each extend between the second input spindle and the second pulley such that the second cable crosses the fourth cable.

16. The medical instrument of claim 9, wherein:
the first cable is directed toward a location on a first side of a central axis of the instrument shaft and the second cable is directed toward a location opposite the first side of the central axis of the instrument shaft.

\* \* \* \* \*